United States Patent [19]

Marsili et al.

[11] 4,226,765
[45] Oct. 7, 1980

[54] NOVEL RIFAMYCIN COMPOUNDS OF HIGH ANTIBIOTIC ACTIVITY

[75] Inventors: Leonardo Marsili; Vittorio Rossetti; Carmine Pasqualucci, all of Milan, Italy

[73] Assignee: Archifar Industrie Chimiche Del Trentino S.p.A., Rovereto, Italy

[21] Appl. No.: 685,624

[22] Filed: May 12, 1976

[30] Foreign Application Priority Data

May 20, 1975 [IT] Italy ................................ 5157 A/75

[51] Int. Cl.$^3$ ............................................ C07D 491/08
[52] U.S. Cl. .............................. 260/239.3 P; 424/244
[58] Field of Search ................................... 260/239.3 P

[56] References Cited

U.S. PATENT DOCUMENTS

| 3,338,888 | 8/1967 | Bickel et al. | 260/239.3 P |
| 3,342,810 | 9/1967 | Maggi et al. | 260/239.3 P |
| 3,738,980 | 6/1973 | Bickel et al. | 260/239.3 P |

OTHER PUBLICATIONS

Handbook of Chemistry and Physics, 45th Ed., C-1, C-5, C-11.
Elderfield et al., "J. Am. Chem. Soc.," vol. 73, pp. 975-984 (1951).
Katritzky et al., "Principles of Heterocyclic Chemistry," (Academic) (1968), p. 158.
Preston, "Chemical Reviews," vol. 74, No. 3, Jun. 1974, pp. 279-284.
Elderfield et al., "J. Am. Chem. Soc.," vol. 70, pp. 44-48 (1948).

*Primary Examiner*—John M. Ford
*Assistant Examiner*—Robert T. Bond
*Attorney, Agent, or Firm*—Oblon, Fisher, Spivak, McClelland & Maier

[57] ABSTRACT

Novel rifamycin compounds of high antibiotic activity. Such compounds are obtained by reacting 3-amino-4-deoxo-4-imino-rifamycin S with aldehydes.

5 Claims, No Drawings

NOVEL RIFAMYCIN COMPOUNDS OF HIGH ANTIBIOTIC ACTIVITY

This invention relates to novel rifamycin compounds of high antibiotic activity, as selected from the group comprising compounds having the following formula:

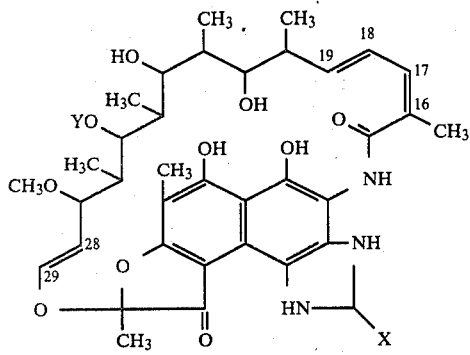

wherein X is a radical selected from the group comprising hydrogen, carboxyl, alkyl with less than 10 atoms C, cycloalkyl with less than 7 atoms C, alkenyl with less than 4 atoms C, cycloalkenyl with less than 7 atoms C, aryl with less than 13 atoms C, arylalkyl with less than 14 atoms C, arylalkenyl with less than 11 atoms C, an heterocycle of 5 and 6 members containing less than 5 eteroatoms selected from the group comprising N, O and S, a condensed heterocycle of 5 and 6 members with an aromatic ring wherein the heterocycle has less than 3 eteroatoms selected from the group comprising O and S, substitution products of the above specified radicals with at least one radical different therefrom and selected from the group comprising, in addition to all of the above specified radicals, halogen, hydroxy, alkoxy, nitro, amino, N-alkylamino, N,N-dialkylamino, formyl, carboxyl, carbalkoxy, carboxyalkoxy, N,N-dialkylaminoalkoxy, acyloxy, acetamido; Y is —H or —COCH$_3$, and its 16, 17, 18, 19 tetrahydroderivatives and 16, 17, 18, 19, 28, 29 hexahydroderivatives and corresponding oxidized products having the formula:

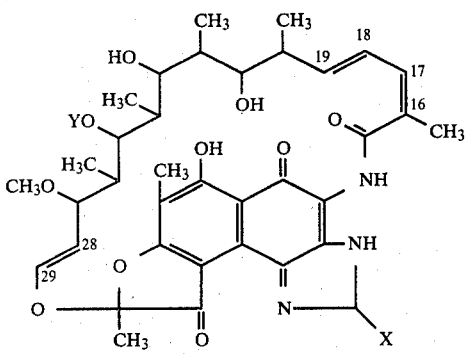

The rifamycin compounds according to the present invention have high antibacterial activity on Gram-positive and Gram-negative bacteria and particularly on Mycobacterium Tuberculosis.

Such compounds are in powder form with a colour from yellow-orange to red-violet, are soluble in most of the organic solvents, such as chlorinated solvents, alcohols, esters, ethers, partially soluble in aromatic hydrocarbons. The compounds of formula (I) are generally soluble in aqueous solutions at pH of between 7 and 7.8, whereas the oxidized derivatives thereof are insoluble in water.

The rifamycin compounds according to the present invention can be prepared from different methods, which are also claimed in this patent. According to a first method, the rifamycin compounds of formula (I) are obtained by reacting a compound having the formula:

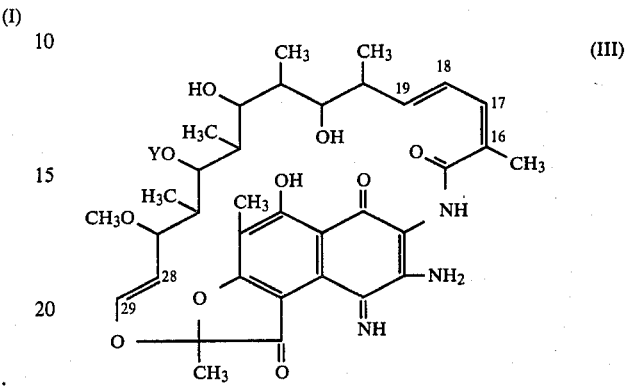

wherein Y is —H or —COCH$_3$, its 16, 17, 18, 19 tetrahydroderivatives and 16, 17, 18, 19, 28, 29 hexahydroderivatives, in the presence of acetic acid and a metal selected from the group comprising zinc and iron, with an aldehyde having the formula:

X—CHO wherein X is as above defined.

The compound of formula (III) is disclosed in a copending patent application Ser. No. 680,771, filed Apr. 27, 1976 to the same applicants.

According to another method, the rifamycin compounds of formula (I) are obtained by reacting 3-aminorifamycin S having the formula:

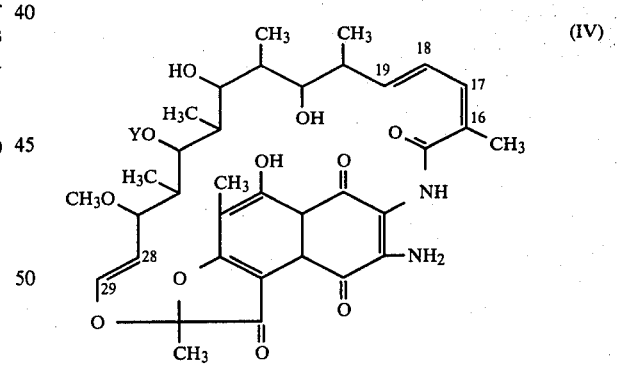

wherein Y is —H or —COCH$_3$, its 16, 17, 18, 19 tetrahydroderivatives and 16, 17, 18, 19, 28, 29 hexahydroderivatives, in a solvent selected from the group comprising ethers and aromatic hydrocarbons, with ammonia gas and an aldehyde having the formula:

X—CHO wherein X is as above defined.

This compound of formula (IV) and its 16, 17, 18, 19 tetrahydroderivatives and 16, 17, 18, 19, 28, 29 hexahydroderivatives is disclosed in the German Pat. No. 1,670,377 and a method of preparing the same is disclosed in the published German Patent Application DOS 2548148, corresponding to applicants' U.S. Pat. application Ser. No. 623,117 filed Oct. 16, 1975.

Finally, according to a further method of preparing a rifamycin compound of formula (I), a compound of formula (III) as above defined, and its 16, 17, 18, 19 tetrahydroderivatives and 16, 17, 18, 19, 28, 29 hexahydroderivatives is reacted in the presence of zinc and acetic acid with a halogen derivative having the formula:

X—CH$_2$—Hal wherein X is as above defined. In order to obtain the oxidized products of formula (II), a compound of formula (I), its 16, 17, 18, 19 tetrahydroderivatives and 16, 17, 18, 19, 28, 29 hexahydroderivatives is oxidized in an inert organic solvent with an oxidizing agent selected from the group comprising potassium ferricyanide, potassium persulphate, manganese dioxide and nitrous acid.

In order that the characteristics of the present invention be more clearly understood, some compounds and method of preparing the same will now be described by way of not limitation in the following examples.

EXAMPLE 1

8 g 3-amino-4-deoxo-4-imino-rifamycin S are dissolved in 15 ml tetrahydrofuran, 5 ml benzaldehyde and 25 ml acetic acid. 1 g zinc is added and the solution is stirred for 10 minutes. The unreacted zinc is filtered and the reaction solution is dropwise poured into a solution of 20 g sodium sulphite in 300 ml water. The precipitate obtained is filtered, washed with water and vacuum dried at 40° C. The product is recristallized from chloroform, thus obtaining 6.5 g of a product of formula I, wherein Y is —COCH$_3$ and X is phenyl. The nuclear magnetic resonance spectrum in CDCl$_3$ shows the most significant peaks at $\delta$: 0.81; 0.92; 1.00; 1.9; 1.97; 2.14; 2.26; 3.02; 3.33; 3.47; 3.59; 3.77; 4.65; 4.75; 4.82; 4.93; 5.06; 5.15; 5.27; 6.22; 6.42; 6.58; and 7.31 p.p.m. and unresolved signals between 7.47 and 8.25 p.p.m. using tetramethylsilane as internal refernece. I.R. spectrum in KBr shows the most significant peaks at 3460; 3360; 3190; 2970; 2930; 2880; 2830; 1710; 1670; 1640; 1600; 1575; 1550; 1528; 1460; 1410; 1370; 1320; 1255; 1242; 1215; 1192; 1160; 1150(sh); 1125; 1095; 1060; 1050(sh); 1020; 975; 945; 920; 880; 798; 780; and 695 cm$^{-1}$.

The electronic absorption spectrum in methanol solution shows peaks at 435; 320 and 265 nm.

EXAMPLE 2

8 g 3-amino-4-deoxo-4-imino-rifamycin S are reacted with 1 g zinc, 7 ml 2-chloro-benzaldehyde and 30 ml 96% acetic acid. After stirring for 10 minutes, at room temperature, excess zinc is filtered and filtrate dropwise poured into 300 ml water containing 20 g sodium sulphite and maintained under strong stirring. The solution is filtered, washed with water and oven dried at 40° C. The product is retaken with 100 ml xylene at 80° C., hot filtered and after 3 hours at room temperature refiltered. The filtrate is concentrated to half volume and allowed to crystallize in refrigerator. After filtering and stove drying, 6.1 g of product of formula I are obtained, in which Y is —COCH$_3$ and X is 2-chlorophenyl. Electronic absorption spectrum in methanol solution shows peaks at 435 nm ($\epsilon_{mol}$=12900); 320(sh) nm and 317 nm ($\epsilon_{mol}$=41700).

I.R. spectrum in nujol shows the most significant peaks at 3375; 3225; 1730(sh); 1715; 1685; 1640; 1605; 1570; 1555; 1530; 1315; 1255; 1235; 1210; 1165; 1100; 1045; 1015; 970; 945; 920; 895; 880; 820; 795; 780; 725 and 685 cm$^{-1}$.

EXAMPLE 3

8 g 3-amino-4-deoxo-4-imino-rifamycin S are reacted with 3 g iron, 9 ml 2-thiophencarboxaldehyde and 30 ml acetic acid. After stirring for 15 minutes at 35° C., excess iron is filtered, the remainder is dropwise added to a solution of 20 g sodium sulphite in 300 ml water under stirring. The precipitate obtained is filtered, washed with water and dried, then recrystallizing from isopropyl ether to obtain 5.1 g product of formula I, in which Y is —COCH$_3$ and X is 2-thienyl. Nuclear magnetic resonance spectrum in CDCl$_3$ shows the most significant peaks at $\theta$: 0.87; 1.00; 1.10; 1.20; 1.87; 1.98; 2.12; 2.27; 3.02; 6.22; 6.42; 6.61; 8.81; 12.50; 12.76 and 13.95 p.p.m., using tetramethylsilane as internal reference. The last four peaks disappear in the presence of deuterated water.

I.R. spectrum in KBr shows the most significant peaks at 3500; 3460; 3350; 3180; 3120; 2970; 2930; 2880; 2830; 1715; 1670; 1640; 1600; 1560; 1525; 1480; 1460; 1410; 1370; 1315; 1255; 1240; 1230; 1210; 1185; 1165; 1145; 1125(sh); 1100; 1050; 1018; 973; 942; 900; 875; 850; 830; 798; 755; 742; 722 and 698 cm$^{-1}$.

Electronic absorption spectrum in methanol solution shows peaks at 440 and 322 nm and a shoulder (sh) at 335 nm.

Similarly, by reacting 3-amino-4-deoxo-4-imino-25-deacetyl-rifamycin S, the corresponding 25-deacetyl-derivative is obtained of the product as defined in the above example.

EXAMPLE 4

8 g 3-amino-4-deoxo-4-imino-rifamycin S are reacted with 1 g zinc, 15 ml dioxane, 25 ml 96% acetic acid, and 1.5 g trioxymethylene. After 30 minutes at 45° C., excess zinc is filtered, the solution is poured into 400 ml water containing 15 g sodium sulphite and the precipitate obtained is filtered. After vacuum drying at 40° C., the product is recrystallized from methyl alcohol, obtaining 3.6 g product of formula I, in which Y is —COCH$_3$ and X is —H.

Electronic absorption spectrum in methanol solution shows peaks at 410 nm ($\epsilon_{mol}$=15400) and 300 nm ($\epsilon_{mol}$=24400).

EXAMPLE 5

8 g 3-amino-4-deoxo-4-imino-rifamycin S are reacted with 1 g zinc, 6 g heliotropin dissolved in 10 ml isopropyl alcohol and 25 acetic acid at room temperature for 10 minutes. Excess zinc is filtered and the solution is poured into 300 ml water containing 18 g sodium sulphite. The precipitate obtained is filtered, washed with water and stove dried at 50° C. The product is recrystallized from chloroform, obtaining 4.9 g of a product of formula I, in which Y is —COCH$_3$ and X is 3,4-methylendioxyphenyl. Electronic absorption spectrum in methanol solution shows peaks at 435 nm ($\epsilon_{mol}$=12900), 320 nm ($\epsilon_{mol}$=41900) and 225 nm ($\epsilon_{mol}$=42400).

Similarly, by reacting 3-amino-4-deoxo-4-imino-16, 17, 18, 19, 28, 29-hexahydro-25-deacetylrifamycin S, 25-deacetyl-16, 17, 18, 19, 28, 29-hexahydroderivative is obtained of the product as defined in the above example.

EXAMPLE 6

1.2 g of the product as obtained in Example 1 are dissolved in 20 ml dichloromethane. The solution is added with 0.5 g manganese dioxide, then stirred for 30 minutes at room temperature. Manganese dioxide is filtered and the solvent is evaporated. 0.8 g of product of formula II are obtained, in which Y is —COCH$_3$ and X is phenyl. I.R. spectrum in KBr shows the most significant peaks at 3460; 3180; 2970; 2930; 2180; 1710; 1665; 1635; 1595; 1525; 1500; 1470; 1455; 1420; 1370; 1305; 1255; 1195; 1180; 1150(sh); 1120; 1075; 1060; 1035; 975; 950(sh); 905; 835; 795; 780; 760; 705; 690 and 660 cm$^{-1}$.

EXAMPLE 7

8 g 3-amino-4-deoxo-4-imino-rifamycin S are reacted with 1 g zinc, 15 ml tetrahydrofuran, 30 ml acetic acid and 5.3 ml heptanal. After stirring for 10 minutes, unreacted zinc is filtered and the solution obtained is dropwise added to a solution of 15 g sodium sulphite in 350 ml water. After vacuum drying at 40° C., the product is recrystallized from ethyl ether, thus obtaining 3.5 g product of formula I, in which Y is —COCH$_3$ and X is 1-hexyl. Electronic absorption spectrum in methanol solution shows peaks at 228, 304 and 415 nm.

EXAMPLE 8

8 g 3-amino-4-deoxo-4-imino-rifamycin S are reacted with 1 g zinc, 5 ml cyclohexanaldehyde, 30 ml acetic acid and 15 ml tetrahydrofuran. After stirring for 30 minutes, unreacted zinc is filtered and the solution poured into 600 ml water containing 15 g sodium sulphite. The precipitate obtained is filtered, washed with water, vacuum dried at 40° C. and suspended in 100 ml ethyl ether. After stirring for 30 minutes, ethyl ether is filtered and solid dissolved in 70 ml methyl alcohol. 0.5 g sodium ascorbate are added, pH is brought to 7.2 by 1% solution sodium hydroxide and then precipitated in 300 ml water. The product is filtered, washed with water and vacuum dried at 40° C. Yield: 6 g compound of formula I, in which Y is —COCH$_3$ and X is cyclohexyl. Electronic absorption spectrum in methanol solution shows peaks at 415 and 300 nm.

EXAMPLE 9

8 g 3-amino-4-deoxo-4-imino-rifamycin S are reacted with 1 g zinc, 15 ml tetrahydrofuran, 5 ml nicotinic aldehyde and 30 ml acetic acid. After stirring for 10 minutes, unreacted zinc is filtered and the solution is dropwise added to 500 ml water containing 15 g sodium sulphite. The precipitate obtained is filtered, washed with water and vacuum dried at 40° C.

The solid is treated with acetone, the undissolved solid is discarded and the solvent evaporated. The residue obtained is heat dissolved in 100 ml benzene, then filtering again after a few hours at +10° C.

Benzene is almost completely evaporated and then the residue is diluted with petroleum ether. After a few minutes, the solution is filtered, yielding 2.5 g compound of formula I, wherein Y is —COCH$_3$ and X is 3-pyridyl.

EXAMPLE 10

8 g 3-amino-4-deoxo-4-imino-rifamycin S are reacted with 1 g zinc, 15 ml tetrahydrofuran, 6.5 g 3,4,5-trimethoxybenzaldehyde and 30 ml acetic acid. The reaction is completed by heating to 50° C. for 20 minutes. The solution is filtered and dropwise added to a solution of 15 g sodium sulphite in 400 ml water. The precipitate obtained is filtered, washed with water and vacuum dried at 40° C. The product is dissolved in the least volume of methyl alcohol, diluted with 200 ml ethyl ether and extracted with a phosphate buffer solution at pH 7.5. The aqueous phase is acidified with diluted hydrochloric acid at pH 4, extracted with chloroform, the solvent is evaporated and the product recrystallized from xylene. Yield: 2.7 g product of formula I, wherein Y is —COCH$_3$ and X is 3,4,5-trimethoxyphenyl.

EXAMPLE 11

8 g 3-amino-4-deoxo-4-imino-rifamycin S are reacted with 1 g zinc, 15 ml tetrahydrofuran, 5 g 2-formilthianaphtene and 25 ml acetic acid. After stirring for 30 minutes at room temperature, unreacted zinc is filtered and the solution is dropwise added to 500 ml water containing 15 g sodium sulphite. The precipitate obtained is filtered, washed with water and vacuum dried at 40° C. The product is then dissolved with ethyl ether and the ether solution is extracted with a phosphate buffer solution at pH 7.5. Next, the aqueous phase is acidified to pH 3 and then extracted with chloroform. The chloroform phase is washed with water and dried and the solvent is evaporated. The residue is recrystallized from cyclohexane, thus obtaining 3.2 g compound of formula I, wherein Y is —COCH$_3$ and X is 2-thianaphtyl. Electronic absorption spectrum in methanol solution shows peaks at 330, 345 and 445 nm.

EXAMPLE 12

8 g 3-amino-4-deoxo-4-imino-rifamycin S are reacted with 1 g zinc, 15 ml tetrahydrofuran, 4.5 g 2-fluoro-6-chlorobenzaldehyde and 25 ml acetic acid. After stirring for 30 minutes at room temperature, unreacted zinc is filtered and filtered solution is dropwise added to 500 ml aqueous solution of 15 g sodium sulphite. The precipitate obtained is filtered, washed with water and vacuum dried at 40° C. Extraction is continuously carried out with ethyl ether and ether solution is washed with phosphate buffer solution at pH 7.5. The aqueous phase is then acidified to pH 3 and extracted with dichloromethane. After washing with water and drying on sodium sulphate, the solvent is evaporated, yielding 3.5 g compound of formula I, wherein Y is —COCH$_3$ and X is 2-fluoro-6-chlorophenyl. Electronic absorption spectrum in methanol solution shows peaks at 312 and 425 nm.

EXAMPLE 13

8 g 3-amino-4-deoxo-4-imino-rifamycin S are reacted with 1 g zinc, 15 ml tetrahydrofuran, 5 g 2-formilphenoxyacetic acid and 25 ml acetic acid. After stirring for 20 minutes at room temperature, unreacted zinc is filtered and the filtered solution precipitated in 500 ml water containing 15 g sodium sulphite. The precipitate obtained is filtered, washed with water and vacuum dried at 40° C. The product is dissolved in 150 ml acetone, the undissolved portion is filtered and diluted with 200 ml ethyl ether. After further filtering, the solvent mixture is evaporated, obtaining 3 g compound of formula I, wherein Y is —COCH$_3$ and X is 2-phenoxyacetic acid.

EXAMPLE 14

8 g 3-amino-4-deoxo-4-imino-rifamycin S are reacted with 1 g zinc, 15 ml tetrahydrofuran, 3.5 g 2-methyl-4-formilthiazole and 25 ml acetic acid. After stirring for 30 minutes at room temperature, the solution is filtered and diluted with 300 ml ethyl ether. The precipitate obtained is dissolved in 100 ml acetic acid and precipitated again with 300 ml water. After filtering, the product is washed with water and dried. 4.5 g compound of formula I are obtained, wherein Y is —COCH$_3$ and X is 2-methyl-4-thiazolyl. Electronic absorption spectrum in methanol solution shows peaks at 315 and 435 nm.

EXAMPLE 15

8 g 3-amino-4-deoxo-4-imino-25-deacetyl-rifamycin S are reacted with 1 g zinc, 5 ml crotonaldehyde and 35 ml acetic acid. After stirring for 10 minutes at room temperature, unreacted zinc is filtered and filtrate is poured into 500 ml water containing 15 g sodium sulphite. The precipitate obtained is filtered and washed with water. After vacuum drying at 40° C., the raw product is dissolved in methyl alcohol, diluted with phosphate buffer solution at pH 7.5 and extracted with benzene. The aqueous phase is acidified to pH 2.5 with diluted hydrochloric acid and the precipitate obtained is filtered and washed with water. 3.7 g product of formula I are obtained, wherein Y is -H and X is 1-propen-1-yl. Electronic absorption spectrum in methanol solution shows peaks at 307, 375 and 425 nm.

EXAMPLE 16

8 g 3-amino-4-deoxo-4-imino-rifamycin S are reacted with 1 g zinc, 15 ml tetrahydrofuran, 3.5 ml 3-cyclohexenaldehyde and 25 ml acetic acid.

After stirring for 3 hours at room temperature, zinc is filtered, the filtered solution is poured into 700 ml water containing 10 g sodium sulphite and the precipitate obtained by filtering is isolated. In accordance with Example 8, 3.3 g product of formula I are then obtained, wherein Y is —COCH$_3$ and X is 3-cyclohexenyl. Electronic absorption spectrum shows peaks at 307 and 417 nm.

EXAMPLE 17

8 g 3-amino-4-deoxo-4-imino-rifamycin S are reacted with 1 g zinc, 15 ml tetrahydrofuran, 5 ml salicyclic aldehyde and 25 ml acetic acid.

After stirring for 1 hour at room temperature, the reaction mixture is treated with 200 ml chloroform, unreacted zinc is filtered, and chloroform phase is washed with aqueous solution of sodium sulphite and then with water. After drying on sodium sulphate, the solvent is evaporated, thus obtaining 3.6 g product of formula I, wherein Y is —COCH$_3$ and X is 2-hydroxyphenyl. Electronic absorption spectrum in methanol solution shows peaks at 333 and 435 nm.

EXAMPLE 18

8 g 3-amino-4-deoxo-4-imino-rifamycin S are reacted with 1 g zinc, 15 ml tetrahydrofuran, 5 g 1-phenyl-5-formil-tetrazole and 25 ml acetic acid. After 2 hours at room temperature, unreacted zinc is filtered and the filtered solution is dropwise added to 500 ml ethyl ether. The solid obtained is dissolved in 500 ml ethyl acetate and the solution is extracted with a phosphate buffer solution at pH 7.5. The aqueous phase is acidified to pH 3 and then extracted again with chloroform. After a final washing with water, the product is dried on sodium sulphate and the solvent is evaporated, thus obtaining 2.7 g compound of formula I, wherein Y is —COCH$_3$ and X is 5(1-phenyl) tetrazolyl.

EXAMPLE 19

8 g 3-amino-4-deoxo-4-imino-rifamycin S are reacted with 1 g zinc, 15 ml tetrahydrofuran, 8 ml cinnamic aldehyde and 30 ml acetic acid. After stirring for 10 minutes at room temperature, unreacted zinc is filtered and the solution is dropwise added to 500 ml water containing 30 g sodium sulphite. The precipitate obtained is filtered, washed with water and vacuum stove dried at 40° C. The residue is dissolved in the least volume of methylisobutylketone and then precipitated with petroleum ether. After filtering, 9 g of a product of formula I are obtained, wherein Y is —COCH$_3$ and X is β-styryl. Electronic absorption spectrum in methanol solution shows peaks at 325, 350 and 437 nm.

EXAMPLE 20

7 g 3-amino-rifamycin S are dissolved in 20 ml tetrahydrofuran, then adding 4 ml benzaldehyde and bubbling ammonia gas for 45 minutes. Further 2 ml benzaldehyde are added, maintaining ammonia gas bubbling for further 60 minutes. The reaction mixture is diluted with 50 ml chloroform, the solution is washed with diluted acetic acid, then with a saturated sodium metabisulphite solution, and finally with water. After drying on sodium sulphate, the chloroform solution is concentrated to half volume and allowed to crystallize overnight at +5° C. The product is filtered, vacuum dried at 40° C., obtaining 5.5 g product identical to that described in Example 1.

EXAMPLE 21

8 g 3-amino-4-deoxo-4-imino-rifamycin S are reacted with 1 g zinc, 50 ml dimethyl sulphoxide, 3.5 ml benzyl bromide and 20 ml acetic acid. The reaction mixture is heated for 2 hours at 60° C. and poured into a mixture of 400 ml ethyl ether and 100 ml methyl alcohol. The mixture is washed with water and then with phosphate buffer solution at pH 7.5. The aqueous phase is acidified to pH 3 and then extracted again with ethyl ether. The solvent is evaporated and the residue is recrystallized from chloroform. 1.2 g of a product identical to that of Example 1 are obtained.

EXAMPLE 22

8 g 3-amino-4-deoxo-4-imino-rifamycin S are reacted with 1 g zinc, 15 ml tetrahydrofuran, 3 g monohydrate glyoxylic acid and 25 ml acetic acid. Unreacted zinc is filtered, the solution is poured into 500 ml water containing 15 g sodium sulphite, the precipitate obtained is filtered and vacuum dried at 40° C. The residue is recrystallized from ethyl ether, thus obtaining 1.8 g product of formula I, wherein Y is —COCH$_3$ and X is —COOH.

EXAMPLE 23

8 g 3-amino-4-deoxo-4-imino-rifamycin S are reacted with 1 g zinc, 25 ml dioxane, 5 g p-nitro-benzaldehyde and 35 ml acetic acid. The reaction mixture is stirred for 30 minutes at 70° C., the unreacted zinc is filtered and the solution is dropwise added to 300 ml water containing 15 g sodium sulphite and 2 g sodium ascorbate. The precipitate obtained is filtered, vacuum dried at 40° C. and recrystallized from xylene. Yield: 3.9 g product of formula I, wherein Y is —COCH$_3$ and X is 4-nitrophenyl. Electronic absorption spectrum in methanol solution shows peaks at 315, 370 and 460 nm. Similarly, by reacting 3-amino-4-deoxo-4-imino-16, 17, 18, 19-tetrahydro-rifamycin S, the corresponding 16, 17, 18, 19 tetrahydroderivative of the product defined in the above example is obtained.

EXAMPLE 24

8 g 3-amino-4-deoxo-4-imino-rifamycin S are reacted with 1 g zinc, 15 ml tetrahydrofuran, 3 ml 5-methyl-2-furylaldehyde and 25 ml acetic acid at 40° C. for 1 hour. Unreacted zinc is filtered, and the solution is poured into 600 ml water containing 15 g sodium sulphite and 2 g sodium ascorbate. The precipitate obtained is filtered, vacuum dried at 40° C. and dissolved in 100 ml methyl alcohol. After diluting with 400 ml ethyl ether, the reaction mixture is extracted with phosphate buffer solution at pH 7.5, the aqueous phase is acidified to pH 3 and extracted again with chloroform. The chloroform phase is further washed with water, dried on sodium sulphate and evaporated to a reduced volume. By precipitation with petroleum ether, 4.8 g compound of formula I are obtained, wherein Y is —$COCH_3$ and X is 2(5-methyl)furyl.

EXAMPLE 25

8 g 3-amino-4-deoxo-4-imino-rifamycin S are reacted with 1 g zinc, 15 ml tetrahydrofuran, 3.2 ml 2-methyl-butanol and 25 ml acetic acid. After stirring for 1 hour at 40° C., unreacted zinc is filtered, the solution is poured into 400 ml ethyl ether and extracted with phosphate buffer solution at pH 7.5. The aqueous solution is acidified to pH 3 and extracted with chloroform. As washed with water, the chloroform solution is dried on sodium sulphate, then evaporated and the residue obtained is crystallized from ethyl ether. Yield: 3.3 g product of formula I, wherein Y is —$COCH_3$ and X is 2-butyl.

EXAMPLE 26

8 g 3-amino-4-deoxy-4-imino-rifamycin S are reacted with 1 g zinc, 15 ml tetrahydrofuran, 4.5 ml 4-isopropyl-benzaldehyde and 25 ml acetic acid at room temperature for 30 minutes. Unreacted zinc is filtered and the solution is poured into 500 ml water containing 15 g sodium sulphite and 0.5 g sodium ascorbate. The precipitate obtained is filtered, washed with water and vacuum dried at 40° C. The residue is recrystallized from a mixture (1:1) of xylene-cyclohexane, thus obtaining 2.9 g product of formula I, wherein Y is —$COCH_3$ and X is 4-isopropylphenyl. Electronic absorption spectrum in methanol solution shows peaks at 315 and 425 nm.

EXAMPLE 27

8 g 3-amino-4-deoxy-4-imino-rifamycin S are reacted with 1 g zinc, 15 ml tetrahydrofuran, 3.5 g 2-fluorobenzaldehyde and 25 ml acetic acid. After stirring for 10 minutes, unreacted zinc is filtered and the solution is poured into 500 ml water containing 15 g sodium sulphite and 1 g sodium ascorbate. The precipitate obtained is filtered, washed with water and vacuum dried at 40° C. By recrystallization from ethyl ether, 3.6 g product of formula I are obtained, wherein Y is —$COCH_3$ and X is 2-fluorophenyl. Electronic absorption spectrum in methanol solution shows peaks at 260, 315 and 420 nm.

EXAMPLE 28

8 g 3-amino-4-deoxy-4-imino-rifamycin S are reacted with 1 g zinc, 15 ml tetrahydrofuran, 4.3 g 3-carbethoxycyclohexanaldehyde and 25 ml acetic acid for 1 hour at room temperature. Unreacted zinc is filtered and the solution is dropwise added to 500 ml water containing 15 g sodium sulphite. The precipitate obtained is filtered, washed with water and vacuum dried at 40' C. By recrystallization from ethyl ether, 5.8 g product of formula I are obtained, wherein Y is —$COCH_3$ and X is 3-carbethoxycyclohexyl. Electronic absorption spectrum in methanol solution shows peaks at 410 and 300 nm.

EXAMPLE 29

8 g 3-amino-4-deoxy-4-imino-rifamycin S are reacted with 1 g zinc, 15 ml tetrahydrofuran, 4.6 g 7-hydroxy-citronellal and 25 ml acetic acid for 1 hour at room temperature. Unreacted zinc is filtered, the solution is dropwise added to 600 ml water containing 10 g sodium sulphite and the precipitate obtained is filtered. After washing with water, the product vacuum dried at 40° C. is stirred in ethyl ether for 30 minutes, then filtered and dried. Yield: 6.2 g product of formula I, wherein Y is —$COCH_3$ and X is 2.6-diimethyl-6-hydroxy-heptyl.

EXAMPLE 30

8 g 3-amino-4-deoxy-4-imino-rifamycin S are reacted with 1 g zinc, 15 ml tetrahydrofuran, 3.5 ml 2-ethyl-butanal and 25 ml acetic acid for 30 minutes at room temperature. Zinc is filtered and the solution is poured into 500 ml water containing 15 g sodium sulphite and 1 g ascorbic acid. The precipitate obtained is filtered, washed with water and vacuum dried at 40° C. The residue is recrystallized from ethyl ether. Yield: 3.8 g product of formula I, wherein Y is —$COCH_3$ and X is 3-pentyl.

EXAMPLE 31

8 g 3-amino-4-deoxy-4-imino-rifamycin S are reacted with 1 g zinc, 15 ml tetrahydrofuran, 5 g 2-carboxybenzaldehyde and 30 ml acetic acid for 30 minutes at room temperature. Unreacted zinc is filtered and the solution is poured into 300 ml chloroform. The reaction mixture is washed with water and dried on sodium sulphate and the solvent is evaporated. The residue is dissolved in 100 ml benzene, added with 0.500 g manganese dioxide and maintained under stirring for 15 minutes at room temperature. After filtering, the benzene phase is extracted with phosphate buffer solution at pH 7.5, the aqueous phase is treated with ascorbic acid and then acidified to pH 3 with diluted hydrochloric acid. The aqueous phase is extracted with dichloromethane, the organic phase is washed with water and dried on sodium sulphate, and the solvent is evaporated. Yield: 2.5 g product of formula I, wherein Y is —$COCH_{13}$ and X is 2-carboxyphenyl.

What we claim is:
1. A rifamycin compound selected from the group comprising compounds having the formula:

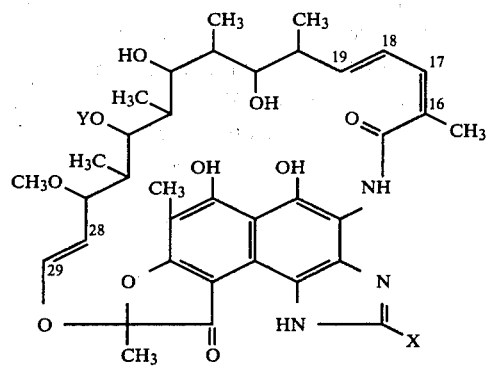

(I)

wherein: X is a radical selected from the group comprising hydrogen, carboxyl, alkyl with less than 10 carbon atoms, cycloalkyl with less than 7 carbon atoms, alkenyl with less than 4 carbon atoms, cycloalkenyl with less than 7 carbon atoms, aryl hydrocarbon with less than 13 carbon atoms, aryl hydrocarbon-alkyl with less than 14 carbon atoms, aryl hydrocarbon-alkenyl with less than 11 carbon atoms, a heterocycle selcted from the group comprising thiophene, furan, thiazole, tetrazole, thionaphtene, methylene dioxyphenyl, and pyridine, substitution products of the above specified radicals with a substituent which is at least one radical different therefrom and selected from the group comprising, in addition to all of the above specified radicals, halogen, hydroxyl, alkoxyl, nitro, amino, N-alkylamino, N,N-dialkylamino, formyl, carboxyl, carboalkoxy, carboxyalkoxy, N,N-dialkylaminoalkoxy, alkanoyloxy and acetamido, there being less than 14 carbon atoms in said radical X; Y is —H or —COCH$_3$, and its 16, 17, 18, 19 tetrahydroderivatives and 16, 17, 18, 19, 28, 29 hexahydroderivatives and corresponding oxidized products having the formula:

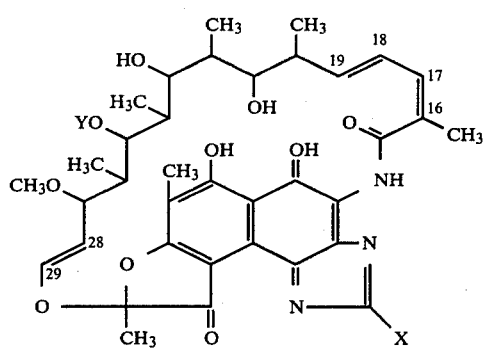

(II)

2. A method of preparing a rifamycin compound, wherein a compound having the formula:

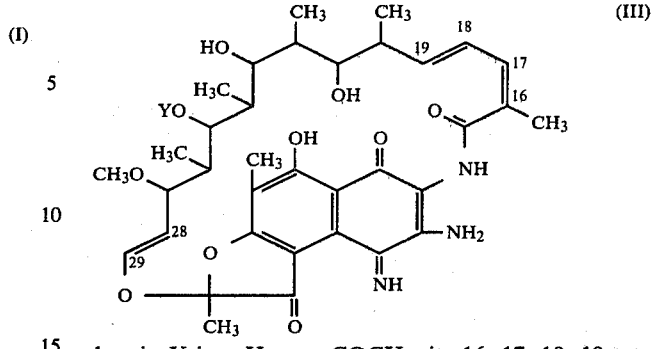

(III)

wherein Y is —H or —COCH$_3$, its 16, 17, 18, 19 tetrahydroderivatives and 16, 17, 18, 19, 28, 29 hexahydroderivatives, is reacted in the presence of acetic acid and a metal selected from the group comprising zinc and iron with an aldehyde having the formula

X—CHO wherein X is a radical selected from the group comprising hydrogen, carboxyl, alkyl with less than 10 carbon atoms, cycloalkyl with less than 7 carbon atoms, alkenyl with less than 4 carbon atoms, cycloalkenyl with less than 7 carbon atoms, aryl hydrocarbon with less than 13 carbon atoms, aryl hydrocarbon-alkyl with less than 14 carbon atoms, aryl hydrocarbon-alkenyl with less than 11 carbon atoms, a hetercycle selected from the group comprising thiophene, furan, thiazole, thionaphtene, methylene dioxphenyl and pyridine, substitution products of the above specified radical with a substituent which is at least one radical different therefrom and selected from the group comprising, in addition to all of the above specified radical, halogen, hydroxyl, alkoxyl, nitro, amino, N-alkylamino, N,N-dialkylamino, formyl, carboxyl, carboalkoxy, carboxyalkoxy, N-N-dialkylaminoalkoxy, alkanoyloxy and acetamido, there being less than 14 carbon atoms in said radical X.

3. A method of preparing a rifamycin compound, wherein 3-amino-rifamycin S having the formula:

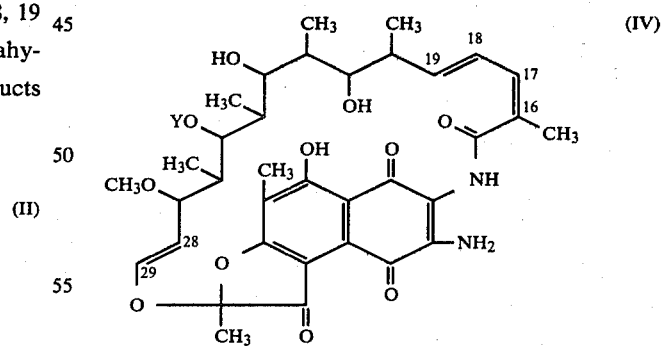

(IV)

wherein Y is —H or —COCH$_3$, its 16, 17, 18, 19 tetrahydroderivatives and 16, 17, 18, 19, 28, 29 hexahydroderivatives, is reacted in a solvent selected from the group comprising ethers and aromatic hydrocarbons with ammonia gas and an aldehyde having the formula:

X—CHO wherein X is a radical selected from the group comprising hydrogen, carboxyl, alkyl with less than 10 carbon atoms, cycloalkyl with less than 7 carbon atoms, alkenyl with less than 4 carbon atoms, cycloalkenyl with less than 7 carbon atoms, aryl hydrocarbon with less than 13 carbon atoms, aryl hydrocarbon-alkyl with less than 14 carbon atoms, aryl hydrocarbon-alkenyl with less than 11 carbon atoms, a hetercycle selected from the group comprising thiophene, furan, thiazole, tetrazole, thionaphtene, methylene dioxyphenyl and pyridine selected from the group comprising, substitution products of the above specified radicals with a substituent which is at least one radical different therefrom and selected from the group comprising, in addition to all of the above specified radicals, halogen, hydroxyl, alkoxyl, nitro, amino, N-alkylamino, N,N-dialkylamino, formyl, carboxyl, carboalkoxy, carboxyalkoxy, N,N-dialkylaminoalkoxy, alkanoyloxy and acetamido, there being less than 14 carbon atoms in said radical X.

4. A method of preparing a rifamycin compound, wherein a compound of formula (III)

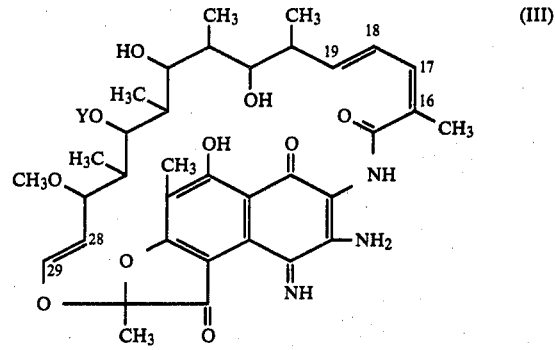

wherein Y is —H or —COCH$_3$. and its 16, 17, 18, 19 tetrahydroderivatives and 16, 17, 18, 19, 28, 29 hexahydroderivatives is reacted in the presence of zinc and acetic acid with a derivative halogen of formula $$X-CH_2-Hal$$

wherein X is a radical selected from the group comprising hydrogen, carboxyl, alkyl with less than 10 carbon atoms, cycloalkyl with less than 7 carbon atoms, alkenyl with less than 4 carbon atoms, cycloalkenyl with less than 7 carbon atoms, aryl hydrocarbon with less than 13 carbon atoms, aryl hydrocarbon-alkyl with less than 14 carbon atoms, aryl hydrocarbon-alkenyl with less than 11 carbon atoms, a hetercycle selected from the group comprising thiophene, furan, thiazole, tetrazole, thionaphtene, methylene dioxyphenl and pyridine, substitution products of the above specified radicals with a substituent which is at least one radical different therefrom and selected from the group comprising, in addition to all of the above specified radical, halogen, hydroxyl, alkoxyl, nitro, amino, N-alkylamino, N,N-dialkylamino, formyl, carboxyl, carboalkoxy, carboxyalkoxy, N,N-dialkylaminoalkoxy, alkanoyloxy and acetamido, there being less than 14 carbon atoms in said radical X.

5. A rifamycin compound which is a product of the process of claim 2.

* * * * *

UNITED STATES PATENT AND TRADEMARK OFFICE
CERTIFICATE OF CORRECTION

PATENT NO. : 4,226,765

DATED : October 7, 1980

INVENTOR(S) : Leonardo Marsili et al

It is certified that error appears in the above—identified patent and that said Letters Patent is hereby corrected as shown below:

On the front page of the Patent, after "Assignee:", delete "Archifar Industrie Chimiche Del Trentino S.p.A.," and insert --Archifar Laboratori Chimico Farmocologici S.p.A.--.

Column 1, in the lower right portion of structural Formula (I), lines 8 through 21, correct the formula as follows:

delete " 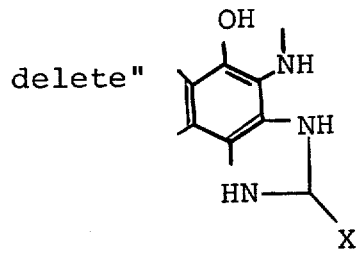 " and insert -- 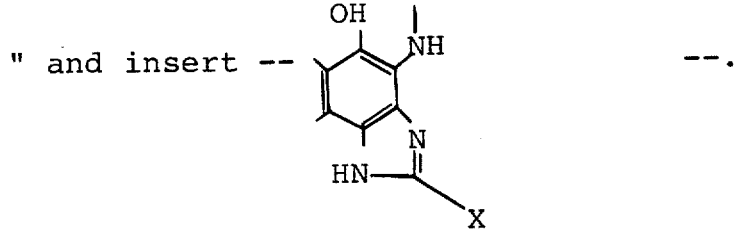 --.

UNITED STATES PATENT AND TRADEMARK OFFICE
CERTIFICATE OF CORRECTION

PATENT NO. : 4,226,765

DATED : October 7, 1980

INVENTOR(S) : Leonardo Marsili et al

It is certified that error appears in the above—identified patent and that said Letters Patent is hereby corrected as shown below:

Column 1, structural Formula (II), lines 44 to 58, correct the lower right portion of the structural formula as follows:

Delete" 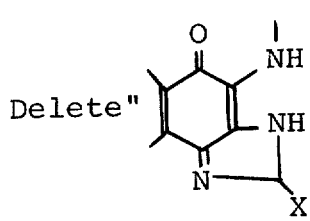 " and insert -- 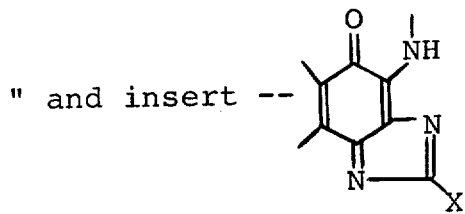 --.

Column 2, structural Formula (IV), lines 40 to 53, correct the lower right portion of the structural formula

UNITED STATES PATENT AND TRADEMARK OFFICE
CERTIFICATE OF CORRECTION

PATENT NO. : 4,226,765

DATED : October 7, 1980

INVENTOR(S) : Leonardo Marsili et al

It is certified that error appears in the above—identified patent and that said Letters Patent is hereby corrected as shown below:

as follows:

delete " 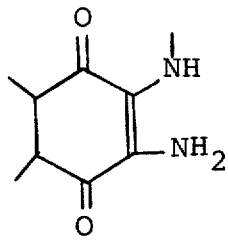 " and insert -- 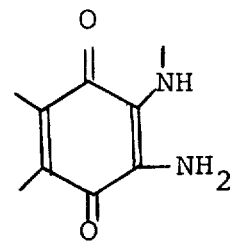 --.

Column 3, line 41, delete "refernece and insert --reference--.

Column 10, line 25, delete "2,6-diimethyl--, and insert therefor --2,6-dimethyl--.

Column 10, line 63, delete "-COCH$_{13}$" and insert therefor --COCH$_3$--.

UNITED STATES PATENT AND TRADEMARK OFFICE
CERTIFICATE OF CORRECTION

PATENT NO. : 4,226,765

DATED : October 7, 1980

INVENTOR(S) : Leonardo Marsili et al

It is certified that error appears in the above—identified patent and that said Letters Patent is hereby corrected as shown below:

Column 11, structural Formula (II), lines 50 to 64, in the lower right portion of the formula delete " 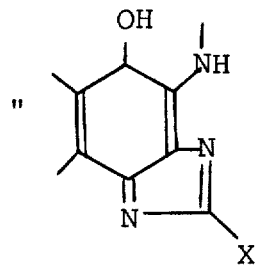 " and insert -- 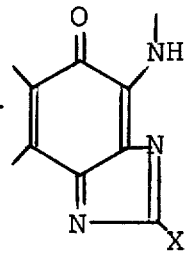 --.

Signed and Sealed this

Eighth Day of December 1981

[SEAL]

Attest:

Attesting Officer

GERALD J. MOSSINGHOFF

Commissioner of Patents and Trademarks